US008122777B2

(12) United States Patent
Greten et al.

(10) Patent No.: US 8,122,777 B2
(45) Date of Patent: Feb. 28, 2012

(54) APPARATUS AND METHOD FOR PRESENTING A PARTICULATE SAMPLE TO THE SCANNING FIELD OF A SENSOR DEVICE

(75) Inventors: Wilhelm G. Greten, Saerbeck (DE); Roland Welle, Steinenstadt (DE)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 12/775,316

(22) Filed: May 6, 2010

(65) Prior Publication Data

US 2010/0212408 A1   Aug. 26, 2010

Related U.S. Application Data

(62) Division of application No. 12/024,548, filed on Feb. 1, 2008, now Pat. No. 7,765,882.

(51) Int. Cl.
  *B01F 15/02* (2006.01)
  *G01N 1/20* (2006.01)
(52) U.S. Cl. ........... 73/863.56; 73/64.56; 73/863.41; 73/863.43; 366/131; 366/136
(58) Field of Classification Search ............ 73/863.41, 73/863.43, 863.44, 863.56, 64.56; 366/108, 366/109, 117, 131, 132, 136, 140, 142, 154, 366/178.1
See application file for complete search history.

(56) References Cited

U.S. PATENT DOCUMENTS

| | | | |
|---|---|---|---|
| 1,958,301 A | 5/1934 | Greene | |
| 2,010,582 A | 8/1935 | Burns et al. | |
| 2,263,790 A | 11/1941 | Vermillion | |
| 2,287,808 A | 6/1942 | Lehde | |
| 2,348,936 A | 5/1944 | Sprenger | |
| 2,787,447 A | 4/1957 | Crawford | |
| 2,879,141 A | 3/1959 | Skeggs | |
| 3,149,650 A * | 9/1964 | Horst | 141/361 |
| 3,250,131 A | 5/1966 | Jordison | |
| 3,326,532 A | 6/1967 | Lodge | |
| 3,663,120 A | 5/1972 | Fortunski | |

(Continued)

FOREIGN PATENT DOCUMENTS

| | | |
|---|---|---|
| EP | 0 388 082 A2 | 9/1990 |
| FR | 2 743 887 A1 | 7/1997 |
| SU | 1177625 A * | 9/1985 |
| WO | WO 00/25110 A1 | 5/2000 |
| WO | WO 01/35720 A1 | 5/2001 |

OTHER PUBLICATIONS

The International Search Report and Written Opinion for International Appl. No. PCT/US2008/052433, mailed Jun. 18, 2008.

*Primary Examiner* — David Rogers
(74) *Attorney, Agent, or Firm* — Alston & Bird LLP

(57) ABSTRACT

A method for presenting various surfaces of particles within a sample to a sensor device is provided. More particularly, embodiments of the present invention provide a method for presenting a sample comprising a plurality of sample particles to a scanning field defined by a sensor device, the method including directing the sample into a scanning chamber configured to contain at least a portion of the scanning field of the sensor device, subjecting the sample to different relative velocities, and redirecting the sample into the scanning chamber such that the plurality of sample particles of the sample are reoriented relative to the scanning field defined by the sensor device. In some embodiments, at least one trait of the sample is measured with the sensor device.

12 Claims, 6 Drawing Sheets

U.S. PATENT DOCUMENTS

| | | | |
|---|---|---|---|
| 3,955,087 A * | 5/1976 | Ashe | 250/360.1 |
| 4,044,617 A | 8/1977 | Mazzetti | |
| 4,896,795 A * | 1/1990 | Ediger et al. | 222/63 |
| 5,409,311 A | 4/1995 | Voss | |
| 5,604,996 A * | 2/1997 | Bestwick et al. | 34/484 |
| 5,934,997 A * | 8/1999 | Nelson et al. | 460/7 |
| 6,192,750 B1 | 2/2001 | Greer et al. | |
| 6,691,563 B1 * | 2/2004 | Trabelsi et al. | 73/73 |
| 2003/0063276 A1 | 4/2003 | Sjodin | |
| 2007/0267409 A1 | 11/2007 | Gard et al. | |

* cited by examiner

APPARATUS AND METHOD FOR PRESENTING A PARTICULATE SAMPLE TO THE SCANNING FIELD OF A SENSOR DEVICE

CROSS-REFERENCE TO RELATED APPLICATIONS

This application is a Divisional of U.S. application Ser. No. 12/024,548, filed Feb. 1, 2008, now U.S. Pat. No. 7,765,882 entitled "Apparatus and Method for Presenting a Particulate Sample to the Scanning Field of a Sensor Device," which is hereby incorporated herein in its entirety.

FIELD OF THE INVENTION

The various embodiments of the present invention relate to the field of seed and grain evaluation systems and more particularly, to systems for presenting substantially all kernels of a sample in various spatial configurations and/or surfaces of individual seeds or grains within a sample to a scanning field of a sensor device.

BACKGROUND OF THE INVENTION

Batch samples of the grains or seeds of some crop plants, such as corn, are often measured and/or evaluated using a sensor device, such as a near-infrared (NIR) spectrometer for example. As one skilled in the art will appreciate, such sensor devices may be capable of evaluating seed or grain traits that are discernible by scanning an outer surface of each seed or grain. Furthermore, there are a number of different traits for which the accurate measurement of all kernels in a sample and a given seed or grain in a sample and in several spatial configurations (i.e. at several points on the surface of each seed) may be important.

For example, the oil content in a sample of corn kernels is distributed substantially homogeneously within the sample. However oil content is only detectable on the germ side of any one particular corn kernel, such that if different sides and/or spatial configurations of each kernel are presented to a sensor device, different oil content results are obtained. Thus, in order to assess oil content in a sample of corn kernels, one must compute an average of oil content measurements obtained over the sample after each kernel has been presented to the sensor device in several different spatial configurations.

In another example, amino acid content in particulate samples (such as corn kernels) is generally present in a low concentration across the sample, such that for a scan of the sample, the signal-to-noise ratio is relatively low. By presenting several surfaces of the kernels in the sample to the sensor device and obtaining an average of the scans of different surfaces (corresponding to different spatial configurations of each kernel), one may substantially increase the signal-to-noise ratio and increase the overall accuracy and precision of amino acid measurements in such a sample. The same principle holds for traits such as "high total fermentables" (HTF) in corn kernel samples without well defined chemical absorption patterns.

In another example, the presence of mold and/or mycotoxins in a particulate sample (such as a batch of corn kernels, for example) may be substantially heterogeneous within the sample (i.e. there are high detectable levels in some kernels and low or non-existent in other kernels). Furthermore, the number of kernels affected to a measurable extent by mold or mycotoxin may be relatively small (even in a large sample size). Thus, in order to detect and/or assess the extent of mold and/or mycotoxin effects in a corn kernel sample, there exists a need to obtain an average measurement across the sample. There further exists a need for a measurement system that may be capable of accepting large sample sizes (to ensure that even small numbers of mold-affected kernels are detected).

In summary, there are a number of different traits for which the accurate measurement of all or most of the seeds or grains in a given sample at several points on the surface of each seed or grain is important. For example, accurate measurement of all the seeds or grains in a sample (at several points on the surface of each seed or grain) may be important for evaluating traits with non-random distribution, low concentration in most seeds or grains, and/or very high concentration in some seeds or grains.

Conventional methods of subjecting several surfaces of each seed or grain within a sample to measurement by an adjacent sensor device involve manually shaking and/or manipulating the seed sample. For example, a technician may scan a small sample of seed or grain using a sensor device, then shake and/or otherwise agitate the sample between scans to rotate or tumble individual seeds within the sample, and finally re-scan the sample to obtain scans of alternate points on the surface of various seeds or grains within the sample. To obtain a statistically significant and/or substantially complete set of sensor measurements for a given sample, the manual rotation/shaking/agitation process is typically repeated many times. Thus, conventional methods for evaluating seed or grain samples using sensor measurements may be very time consuming, result in generally low throughput, and may often lead to incomplete sampling and/or flawed data. Furthermore, conventional methods for mixing samples such that each kernel and/or seed within the sample is presented to a sensor device in several spatial configurations do not allow for the accommodation of different and/or very large sample sizes. Thus, conventional mixing and/or presentation methods may not allow for the detection of traits that are present only in a few representative particles of a relatively large sample (having hundreds or thousands of particles, for example).

Therefore, in order to facilitate faster and substantially complete scanning of a sample of seeds or grains (using a sensor such as an NIR spectrometer for example) in several spatial configurations there exists a need in the art for an apparatus that effectively and systematically presents several surfaces of individual seeds or grains within a sample to a scanning area spanned by a sensor device. There also exists a need for a system, device, and method that allows for the fast, accurate, and complete measurement of the traits of substantially all (or at least a statistically-significant sample thereof) of the seeds or grains in a sample while continuously adjusting the spatial configurations of each seed or grain in the scanning area. There further exists a need for a system, device, and method satisfying the needs listed above that accommodates variable and/or relatively large sample sizes such that relatively rare traits may be accurately identified and/or quantified within a sample.

SUMMARY OF THE INVENTION

The embodiments of the present invention satisfy the needs listed above and provide other advantages as described below. Embodiments of the present invention may include an apparatus for presenting a sample (comprising a plurality of sample particles, for example) to a scanning field defined by a sensor device. Some apparatus embodiments may comprise a sensor device capable of defining a scanning field for scanning and/or imaging the sample. According to such embodiments, the sensor device may include, but is not limited to a near-infrared (NIR) spectrometer.

In one embodiment, a method is provided for presenting a sample comprising a plurality of sample particles to a scanning field defined by a sensor device, the method comprising directing a sample into a scanning chamber configured to contain at least a portion of the scanning field of the sensor device, subjecting the sample to different relative velocities, and redirecting the sample into the scanning chamber such that the plurality of sample particles of the sample are reoriented relative to the scanning field defined by the sensor device. In some embodiments, subjecting the sample to different relative velocities may comprise subjecting portions of the sample to at least first and second velocities. In some embodiments, the first and second velocities may be first and second velocities having different relative speeds and/or first and second velocities having different relative directions. In some embodiments, the first and second velocities may comprise velocities having substantially the same direction and different speeds, in other embodiments, the first and second velocities may comprise velocities having substantially the same speed and different directions. In some embodiments, subjecting the sample to different relative velocities may comprise moving at least a portion of the sample past a substantially stationary object. In other embodiments, subjecting the sample to different relative velocities may comprise moving at least one object through a substantially stationary portion of the sample.

Another method embodiment is directed to processing a sample comprising a plurality of sample particles. In one embodiment, the method comprises directing the sample into a scanning chamber configured to contain at least a portion of the scanning field of the sensor device, subjecting the sample to different relative velocities, redirecting the sample into the scanning chamber such that the plurality of sample particles of the sample are reoriented relative to the scanning field defined by the sensor device, and measuring at least one trait of the sample with the sensor device. In some embodiments, the at least one trait may include oil content of the sample particles, amino acid content of the sample particles, protein content of the sample particles, protein quality of the sample particles, high total fermentables of the sample particles, a presence of mold in the sample particles, and/or a presence of mycotoxins in the sample particles, or any combinations thereof. Embodiments may also further comprise collecting sample data, evaluating the sample, or selecting samples having desired genotypes, based at least in part on the at least one trait.

Another embodiment is directed to an apparatus for presenting a sample comprising a plurality of sample particles to a scanning field defined by a sensor device, the apparatus comprising a first rotating surface configured to rotate about a central axis in a first direction and a second rotating surface disposed radially inward from the first rotating surface and configured to rotate about the central axis in a second direction opposite the first direction. Furthermore, the second rotating surface comprises an inner wall member extending substantially vertically from a radially-inward edge of the second rotating surface. In some embodiments, the first and second rotating surfaces may be further configured to rotate about a central axis at a first and second speed, respectively. In some such embodiments the first speed may be equivalent to the second speed. In other embodiments, the first speed may be selectively greater than and/or less than the second speed. Furthermore, in some embodiments, at least one of the first rotating surface and the second rotating surface may comprise a non-skid surface such that the sample is less likely to slip relative to the moving first and/or second rotating surfaces.

The apparatus further comprises a dividing member fixedly disposed radially between the first rotating surface and the second rotating surface, wherein the dividing member has an entrance end and an exit end. The dividing member may be configured to cooperate with the second rotating surface and the inner wall member thereof to define a scanning chamber configured to contain at least a portion of the scanning field of the sensor device. The apparatus further comprises an entrance gate disposed adjacent to the entrance end of the dividing member and disposed substantially vertically with respect to the first rotating surface. The entrance gate is configured for directing the sample from the first rotating surface to the second rotating surface and into the scanning chamber. The apparatus further comprises an exit gate disposed adjacent to the exit end of the dividing member and disposed substantially vertically with respect to the second rotating surface. The exit gate may be configured for directing the sample from the second rotating surface to the first rotating surface and out of the scanning chamber. Thus, the various embodiments of the present invention may be capable of continuously reorienting the plurality of sample particles of the sample relative to the scanning field defined by the sensor device as the sample is directed into and out of the scanning chamber.

In some apparatus embodiments at least one of the entrance and exit gates may be operably engaged with support member extending radially outward from the central axis above an upper edge of the inner wall member, the support member may thereby be configured to secure the entrance and exit gates in a fixed position relative to the first and second rotating surfaces, respectively. Furthermore, in such embodiments, the support member operably engaged with at least one of the entrance and exit gates may be configured to be selectively movable about the central axis such that the angular positions of the entrance and/or exit gates relative to the central axis may be at least partially adjustable.

According to some embodiments, the apparatus may further comprise a leveling device operably engaged between the divider member and the inner wall member such that the leveling device extends at least partially through the scanning chamber. Thus, in such embodiments, the leveling device may be configured to arrange the plurality of particles in the sample to form a substantially flat upper sample surface as the sample is directed through the scanning chamber.

Furthermore, some apparatus embodiments may further comprise an outer wall member extending substantially vertically from a radially-outward edge of the first rotating surface. According to some such embodiments, the outer wall member may define an emptying aperture. Such embodiments may further comprise a door member configured for selectively opening the emptying aperture and for deflecting the particles of the sample outward through the emptying aperture.

Other embodiments provide particular methods for presenting a sample comprising a plurality of sample particles to a scanning field defined by a sensor device. In one embodiment, the method comprises steps for rotating a first rotating surface about a central axis in a first direction, and rotating a second rotating surface about the central axis in a second direction opposite the first direction. The second rotating surface may be disposed radially inward from the first rotating surface. Furthermore, the second rotating surface comprises an inner wall member extending substantially vertically from a radially-inward edge of the second rotating surface. The method further comprises fixing a dividing member radially between the first rotating surface and the second rotating surface, wherein the dividing member includes an entrance end and an exit end. The dividing member may be configured to cooperate with the second rotating surface and the inner wall member thereof to define a scanning chamber configured to contain at least a portion of the scanning field of the sensor device. The method further comprises directing the sample from the rotating surface to the second rotating surface and into the scanning chamber using an entrance gate disposed adjacent to the entrance end of the dividing member. As described herein with respect to the various apparatus embodiments of the present invention, the entrance gate may be disposed substantially vertically with respect to the first rotating surface. The method may further comprise directing the sample from the second rotating surface to the first rotating surface and out of the scanning chamber using an exit gate disposed adjacent to the exit end of the dividing member. As further described herein, the exit gate may be disposed substantially vertically with respect to the second rotating surface. Thus according to various method embodiments, the plurality of sample particles of the sample may be continuously reoriented relative to the scanning field defined by the sensor device as the sample is directed into and out of the scanning chamber by the entrance and exit gates, respectively.

Thus, various embodiments of the apparatus and method for presenting a sample to a scanning field defined by a sensor device may provide one or more advantages that may include, for example: providing an apparatus and method capable of continuously reorienting individual particles of a sample in a scanning field of a sensor device; providing for the rapid and substantially continuous recycling of a particulate sample through a scanning field of a sensor device so as to be capable of efficiently obtaining a statistically-significant number of scans for several points on the surfaces of a plurality of particles within a sample; and providing a sample presentation apparatus capable of handling, recycling, and continuously reorienting a sample containing a large number of individual particles.

BRIEF DESCRIPTION OF THE DRAWINGS

Figure 1:
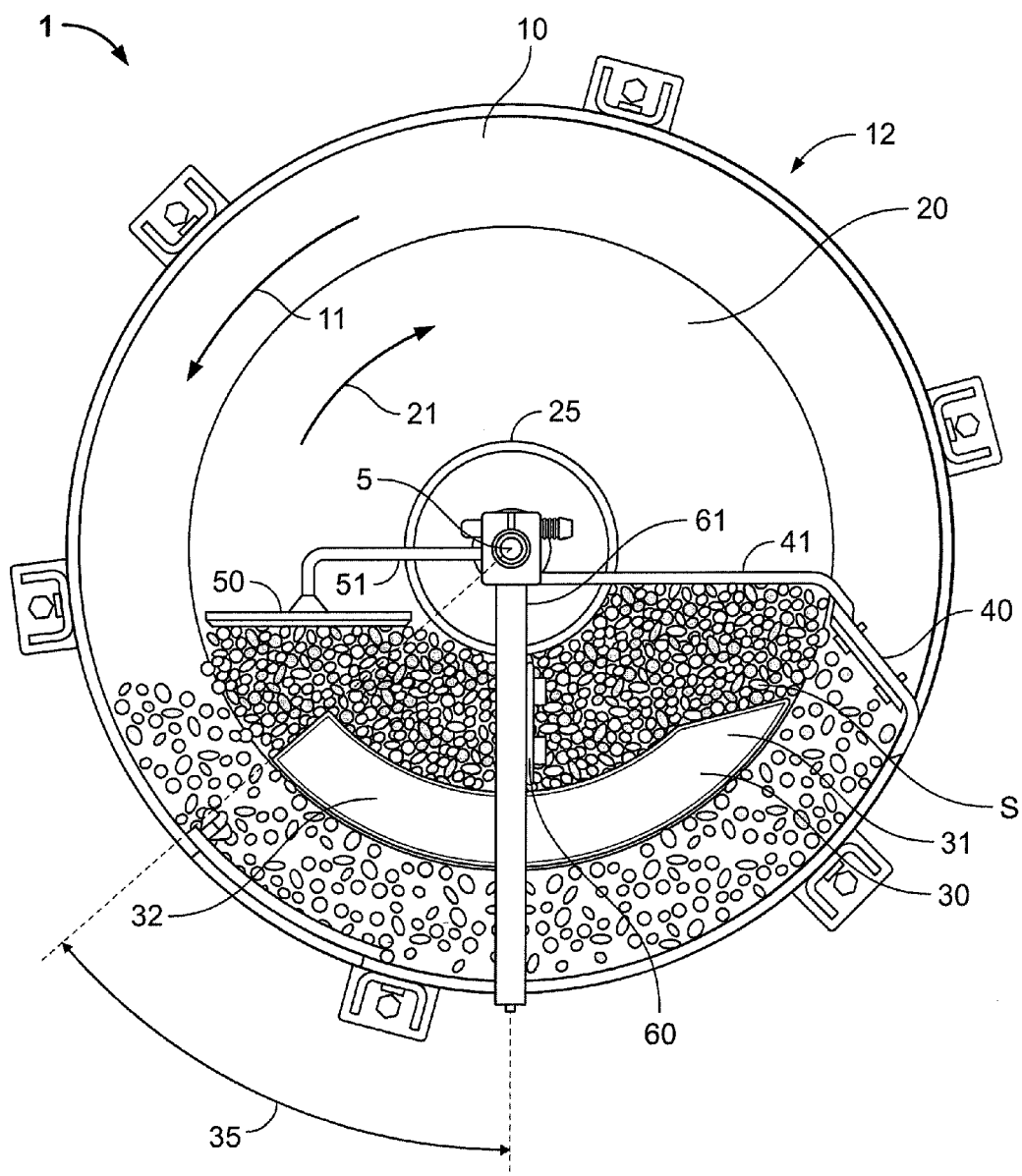
Figure 2:
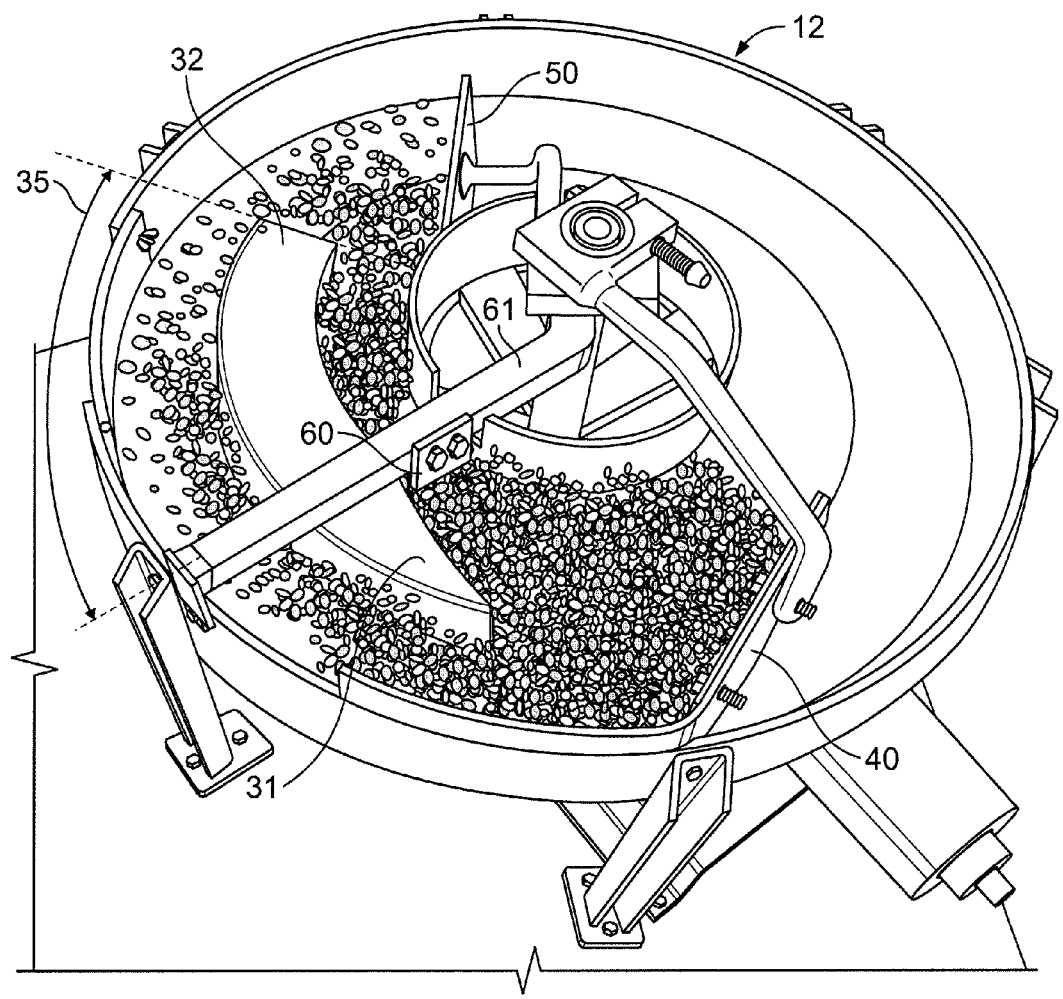
Figure 3:
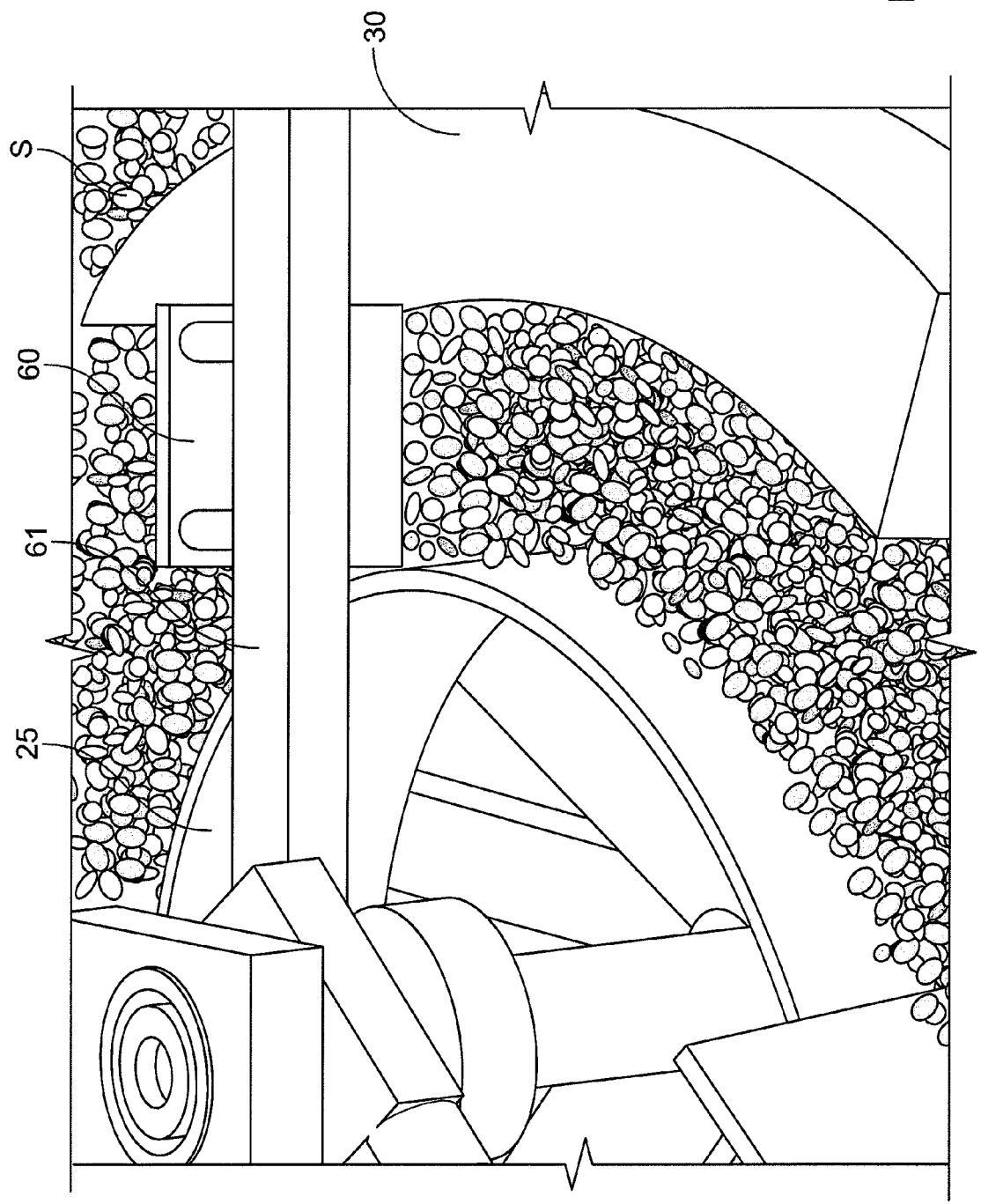
Figure 4:
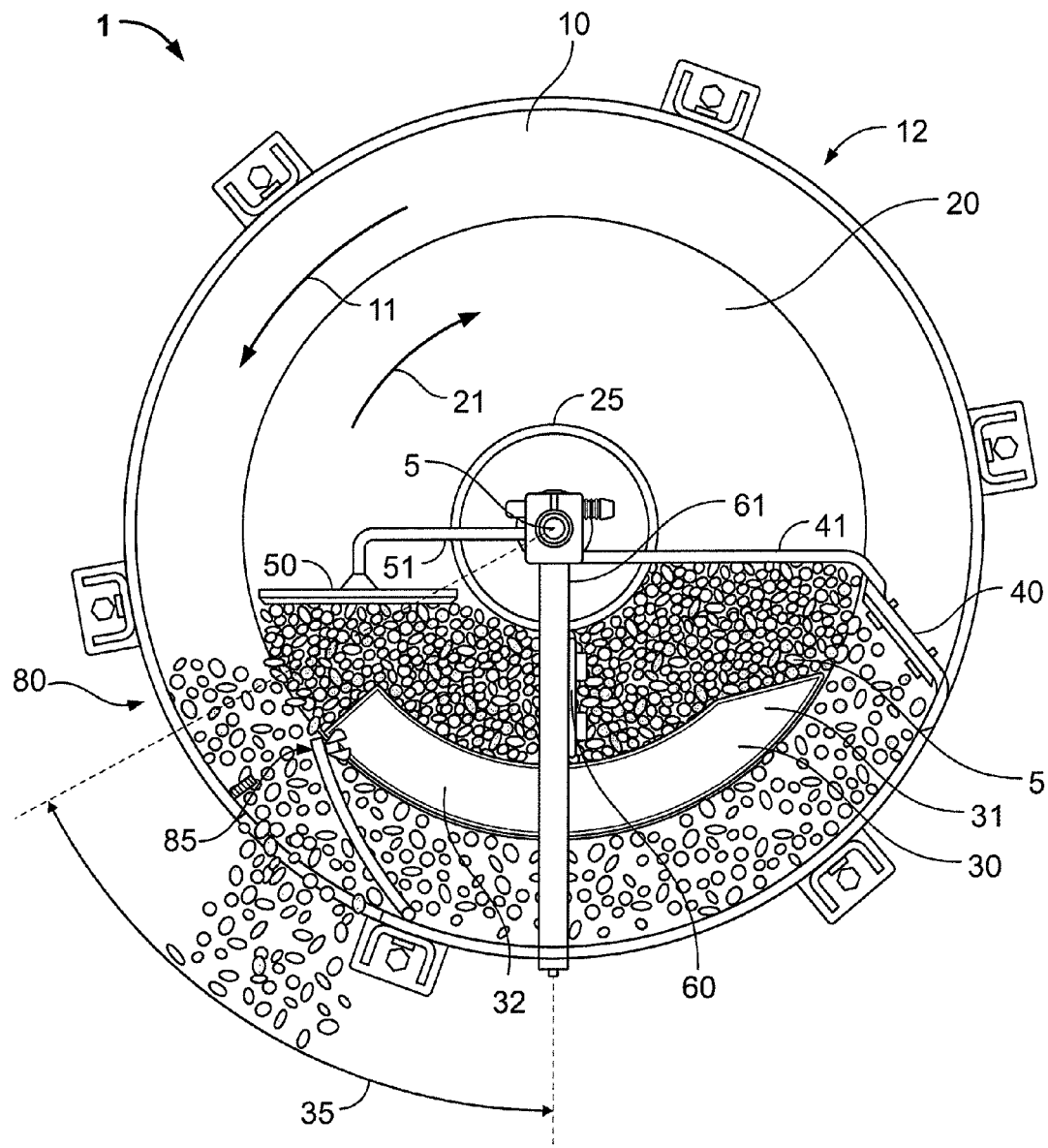
Figure 5A:
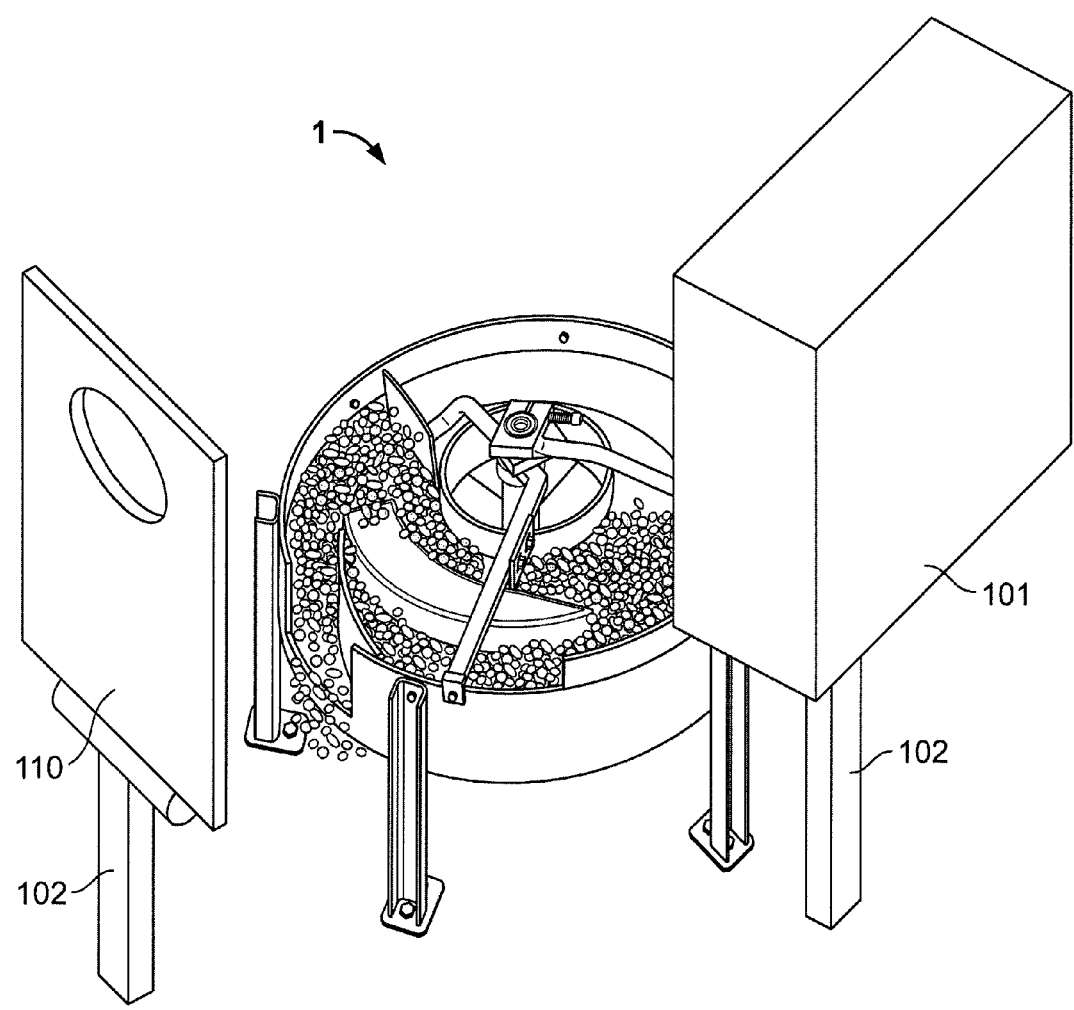
Figure 5B:
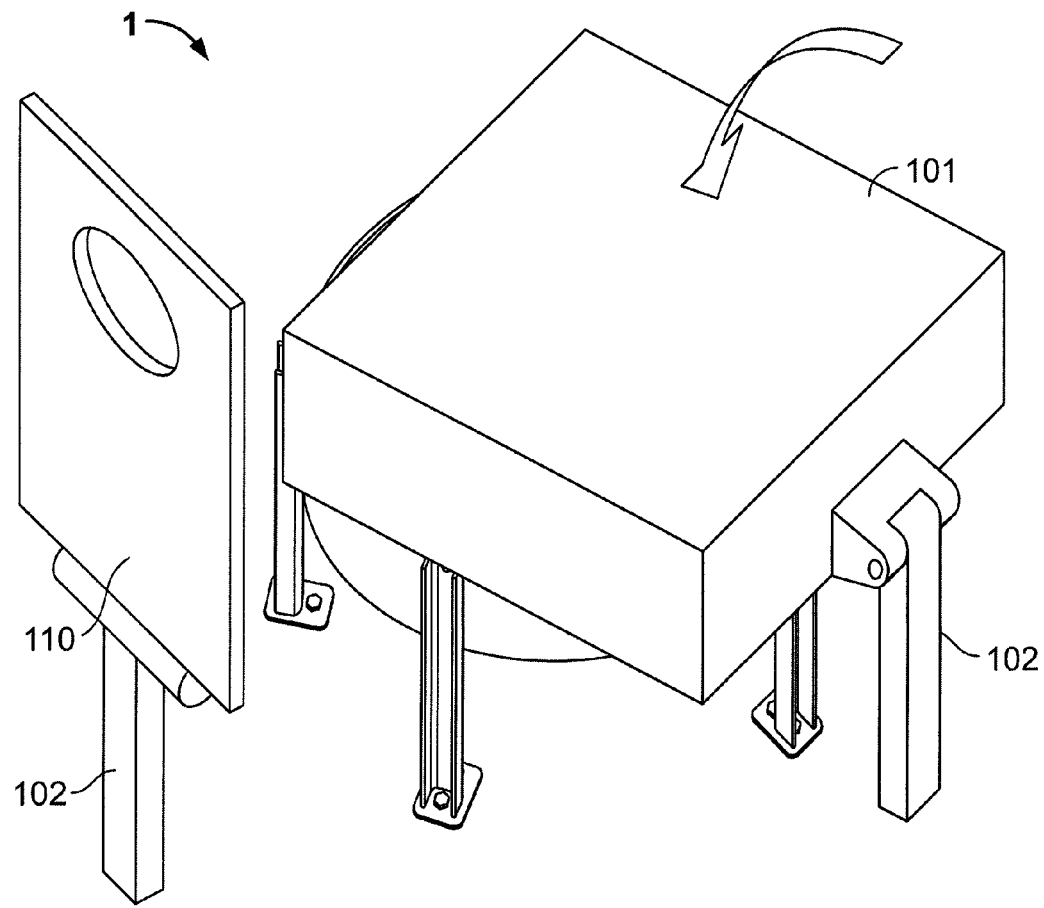

Having thus described the invention in general terms, reference will now be made to the accompanying drawings, which are not necessarily drawn to scale, and wherein:

FIG. 1 shows a non-limiting top-view schematic of an apparatus for presenting a sample comprising a plurality of sample particles to a scanning field defined by a sensor device, according to one embodiment of the present invention;

FIG. 2 shows a non-limiting top perspective view of an apparatus for presenting a sample comprising a plurality of sample particles to a scanning field defined by a sensor device, according to one embodiment of the present invention;

FIG. 3 shows a non-limiting detailed perspective view of an apparatus, according to one embodiment of the present invention, showing a sample comprising a plurality of sample particles entering a scanning chamber defined between a dividing member, inner wall member, and a leveling device operably engaged between the divider member and the inner wall member;

FIG. 4 shows a non-limiting detailed top-view schematic of an apparatus, according to one embodiment of the present invention, showing the sample comprising a plurality of sample particles being emptied from the apparatus via an emptying aperture; and FIG. 5A shows a non-limiting perspective view of a scanning apparatus, according to one embodiment of the present invention including a sensor device in a raised position relative to a scanning field defined between a divider member and an inner wall member such that the scanning apparatus may be filled with a sample comprising a plurality of sample particles; and FIG. 5B shows a non-limiting perspective view of a scanning apparatus, according to one embodiment of the present invention including a sensor device engaged in a scanning position relative to a scanning field defined between a divider member and an inner wall member of the apparatus.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

While the various apparatus 1 and method embodiments of the present invention are described herein with respect to the presentation of a sample S comprising a plurality of grain and/or corn kernels to a scanning field defined by a sensor device 101 comprising a spectrometer (such as an NIR spectrometer), it should be understood that embodiments of the present invention may be used to continuously re-circulate and present various surfaces of a variety of different particle types to a number of different sensor devices. For example, in some embodiments, the apparatus 1 of the present invention may be used to present various surfaces of substantially regularly-shaped particles (such as pharmaceutical tablets, for example) to a quality-control scanning device (such as an optical scanner).

It should also be noted that although the present specification and appended drawings show and describe a specific embodiment of the present invention, other embodiments of the present invention may comprise any apparatus or method configured to subject a sample comprising a plurality of sample particles to different relative velocities so as to reorient the sample particles to a scanning area defined by a scanning device. In various embodiments, this may comprise, but need not be limited to, moving an object or structure through a substantially stationary seed mass, moving at least a portion of the sample past a substantially stationary object or structure, moving portions of the sample in the same direction at different speeds, and/or moving portions of sample in different directions. For the purposes of the present specification and appended drawings and claims, the term "velocity" and other forms thereof may refer to any form of velocity, including, but not limited to, linear, rotational, or angular speed. In some, but not all forms, the term may comprise speed and direction. Thus, for example, the term relative velocity and other forms thereof may comprise relative speeds or relative directions or any combinations thereof.

In various embodiments, a sample may be processed by being presented to one or more sensor devices in order to measure one or more traits of the sample. In various embodiments, processing may comprise, but need not be limited to, collecting sample data, evaluating the sample, or selecting a sample (or portions of a sample) having a desired genotype, based at least in part on at least one trait. With regard to those embodiments that process seed samples, these traits may include, but need not be limited to, oil content, amino acid content, protein content, protein quality, a presence of mold, a presence of mycotoxins, etc.

FIG. 1 shows a top view of one embodiment of an apparatus for presenting a sample S (comprising a plurality of sample particles, such as kernels of grain, for example) to a scanning field defined by a sensor device 101 (see FIG. 5B showing a sensor device 101 comprising a near-infrared (NIR) spectrometer disposed adjacent to a scanning chamber 35 defined by the apparatus 1). In one embodiment, as shown in FIG. 1, the apparatus 1 comprises a first rotating surface 10 configured to rotate about a central axis 5 in a first direction 11. The apparatus 1 further comprises a second rotating surface 20 disposed radially inward from the first rotating surface 10 and configured to rotate about the central axis 5 in a second direction 21 opposite the first direction 11. In some embodiments, the second rotating surface 20 may comprise an inner wall member 25 extending substantially vertically from a radially-inward edge of the second rotating surface 20 (see also, FIGS. 2 and 3). While the embodiments shown in FIGS. 2 and 3 depict an inner wall member 25 operably engaged with the second rotating surface 20 such that the inner wall member 25 rotates in the second direction 21 along with the second rotating surface 20, it should be understood that, in some apparatus 1 embodiments, the inner wall member 25 may be configured to remain stationary relative to the central axis 5 as the second rotating surface 20 rotates in the second direction 21.

As shown in FIG. 1, the apparatus 1 further comprises a dividing member 30 fixedly disposed radially between the first rotating surface 10 and the second rotating surface 20. The dividing member 30 includes an entrance end 31 and an exit end 32. Furthermore, the dividing member 30 may be configured to cooperate with the second rotating surface 20 and the inner wall member 25 to define a scanning chamber 35 configured to contain at least a portion of the scanning field of the sensor device 101 as the sensor device is positioned relative to the apparatus 1 (see FIG. 5B, for example). It should be understood that, in some alternative embodiments, the scanning chamber 35 may also be defined on the first (and radially-outward) rotating surface 10 between the dividing member 30 and the outer wall 12. According to such embodiments, the leveling device 60 (described further herein) may be operably engaged with a support member 61 extending over the scanning chamber 35 near the entrance end 31 of the divider member 30 and over the first rotating surface 10.

In order to direct the various particles of the sample into the scanning chamber 35, the apparatus 1 further comprises an entrance gate 40 disposed adjacent to the entrance end 31 of the dividing member 30. The entrance gate 40 may be disposed substantially vertically with respect to the first rotating surface 10 and is configured for directing the sample S (and/or particles thereof) from the first rotating surface 10 to the second rotating surface 20 and into the scanning chamber 35. As shown in FIG. 1, the entrance gate 40 may be disposed at an angle relative to a radius extending outward from the central axis 5 so as to be more readily capable of re-directing the sample S (i.e. directing the sample S from the first rotating surface 10 to the second rotating surface 20 (about the entrance end 31 of the dividing member 30) and into the scanning chamber 35).

Thus, as the sample S is carried about the apparatus 1 by the rotation of the first rotating surface 10 in the first direction 11, the entrance gate 40 may at least temporarily halt the progress of the sample S in the first direction 11 and direct the various particles of the sample S onto the second rotating surface 20 (which, as described herein, is configured to rotate about the central axis 5 in a second direction 21 substantially opposite the first direction 11). Therefore, the change in direction of the sample S at the entrance gate 40 may impart a tumbling motion and/or rotation to at least some of the particles of the sample S as they enter the scanning chamber 35 such that multiple surfaces of each particle in the sample S may be presented to the scanning field of the sensor device 101 (which, in some embodiments, as shown generally in FIG. 5B may be positioned substantially above the scanning chamber 35 defined by the apparatus 1 embodiments of the present invention). Because each cycle of the sample S through the scanning chamber 35 results in a different group of individual particles rising to the "top" of the sample S in the scanning chamber 35, and because the counter-rotation of the rotating surfaces 10, 20 re-circulates and reorients the individual sample particles, the apparatus 1 may thus ensure that a statistically significant number of scans are obtained for at least a majority of the individual particles at multiple locations on the surface of the scanned particles. It should be understood that the sensor device 101 may comprise a controller element (not shown), such as that provided in the CORA 45 NIR Spectrometer system available from Carl Zeiss, AG, configured for determining a number of recirculation cycles through the scanning chamber 35 are required to obtain a statistically significant number of scans to characterize the sample S adequately for a given experimental task (i.e. the quantification of the prevalence of a trait of interest in a given sample S). In other embodiments, a user may place a series of particles having contrasting colors (such as a small number of red particles in a larger sample of otherwise yellow particles) in the apparatus 1 and observe the number of times the particles having contrasting colors appear at the top of the scanning chamber 35 (and thereby in the scanning field of the sensor device 101). Such calibration methods may allow the user to determine a characteristic time (given a particular sample size) that the apparatus must run in order to ensure that each particle within a sample is presented to the scanning field of the sensor device 101 for a selected number of times.

According to various apparatus 1 embodiments of the present invention, the first and second rotating surfaces 10, 20 may be configured to counter-rotate at a first and second speed, respectively. In some embodiments, the first and second speeds of the first and second rotating surfaces 10, 20 may be substantially equal. However, in some apparatus embodiments, it may be advantageous to adjust a difference in speeds of the first and second rotating surfaces 10, 20. According to such embodiments, the apparatus 1 may further comprise a controller element (not shown) in communication with a motor (such as an electric motor, for example) configured to drive at least one of the first and second rotating surfaces 10, 20. According to such embodiments, the controller element may comprise a user interface configured to receive a user input for controlling one or more of the first and second speeds of the first and second rotating surfaces 10, 20, respectively. Thus, in some embodiments, the first speed may be equivalent to the second speed. In other embodiments, the first speed may be greater than the second speed. In other embodiments, the first speed may be less than the second speed. Furthermore, according to various embodiments, one or both of the first and second rotating surfaces 10, 20 may comprise a non-skid surface. It should be understood that in such embodiments, the non-skid surface may be applied by adding a polymeric, composite, and/or metallic coating to the rotating surfaces 10, 20. In other embodiments, the rotating surfaces 10, 20 may be scored, etched, sanded, and/or chemically treated to provide a substantially non-skid surface such that the sample particles of the sample S may be carried on the rotating surfaces 10, 20 at near or equal to the first and second speeds, respectively without substantial slippage due to centrifugal forces generated in the apparatus.

In order to re-circulate the various particles of the sample S after they have passed at least once through the scanning chamber 35, the various apparatus 1 embodiments of the present invention (as shown, for example, in FIG. 1) may further comprise an exit gate 50 disposed adjacent to the exit end 32 of the dividing member 30. The exit gate 50 may be disposed substantially vertically with respect to the second rotating surface 20 and configured for directing the sample S from the second rotating surface 20 to the first rotating surface 10 and out of the scanning chamber 35 (see FIG. 1, showing the general path of recirculation of the sample S in and out of the scanning chamber 35 via the cooperation of the entrance gate 40, the dividing member 30, and the exit gate 50). As shown in FIG. 1, the exit gate 50 may be disposed at an angle relative to a radius extending outward from the central axis 5 so as to be more readily capable of directing the sample S from the second rotating surface 20 to the first rotating surface 10 and out of the scanning chamber 35. Thus, as described further herein, the plurality of sample particles of the sample S are continuously reoriented relative to the scanning field defined by the sensor device 101 as the various sample particles of the sample S are directed into and out of the scanning chamber 35.

As shown in FIG. 2, various apparatus 1 embodiments may further comprise a leveling device 60 operably engaged between the divider member 30 and the inner wall member 25. For example, the leveling device 60 may comprise a substantially planar plate member (as shown in FIG. 2, for example) operably engaged with a support member 61 extending over the scanning chamber 35 near the entrance end 31 of the divider member 30. Thus, as shown in FIG. 3, the leveling device 60 may thereby extend at least partially through the scanning chamber 35 such that the leveling device 60 may be configured to arrange the plurality of particles in the sample S to form a substantially flat upper sample surface as the sample S is directed through the scanning chamber 35. For example, as shown generally in FIG. 2, a lower edge of the substantially planar leveling device 60 may act to "flatten" the profile of a group of sample particles as they are directed through the scanning chamber 35. Thus, the leveling device 60 may ensure that the various surfaces of the individual particles of the sample S are positioned at an optimal distance from the scanning element or other sensing element of the sensor device 101 as the sample S is directed through the scanning chamber 35. According to various apparatus 1 embodiments, the leveling device 60 may be selectively and/or adjustably engaged with the support member 61 extending above the scanning chamber 35 such that a lower edge of the leveling device 60 may be adjusted to be closer to and/or farther away from the second rotating surface 20. Thus, according to such embodiments, an optimal level of the sample S may be adjusted according to the requirements of each particular sample S and/or to suit the optimal operating characteristics of the sensor device 101 that may be used to scan and/or image the various sample particles of the sample S as it is directed through the scanning chamber 35.

According to various apparatus 1 embodiments of the present invention, the positions of the entrance gate 40 and exit gate 50 may be substantially adjustable about the central axis 5 of the apparatus 1. For example, in some embodiments, the apparatus 1 may further comprise a support member 41 extending radially outward from the central axis 5 (i.e. from a central shaft of the apparatus 1) above an upper edge of the inner wall member 25. The support member 41 may be operably engaged with the entrance gate 40 and configured to secure the entrance gate 40 in a fixed position relative to the first rotating surface 10 (as shown generally in FIG. 1). In some such embodiments, the support member 41 may be configured to be selectively movable about the central axis 5 such that an angular position of the entrance gate 40 relative to the central axis 5 is adjustable. Furthermore, the apparatus 1 may also comprise a support member 51 extending radially outward from the central axis 5 above an upper edge of the inner wall member 25. The support member 51 may be operably engaged with the exit gate 50 and configured to secure the exit gate 50 in a fixed position relative to the second rotating surface 20. As described herein with respect to the entrance gate support member 41, the exit gate support member 51 may be configured to be selectively movable about the central axis 5 such that an angular position of the exit gate 50 relative to the central axis 5 is adjustable. In some embodiments, the support members 41, 51 (and 61, where applicable) may be operably engaged with a central shaft and/or a stationary central post extending through the central axis 5 of the apparatus 1 via one or more collar and set-screw devices that may be selectively loosened so that the support members 41, 51, 61 (and consequently the gates 40, 50 and leveling device 60) may be selectively moved about the central axis 5 to a selected angular position relative to the apparatus 1 (and/or relative to the dividing member 30 thereof, for example).

As shown in FIG. 1, various apparatus 1 embodiments may further comprise an outer wall member 12 extending substantially vertically from a radially-outward edge of the first rotating surface 10. According to some embodiments, the outer wall member 12 may separate from the first rotating surface 10 such that the outer wall member 12 may be fixed (i.e. non-rotating) relative to the central axis 5. In other apparatus 1 embodiments, the outer wall member 12 may be attached to the first rotating surface 10 and therefore rotate therewith in the first direction 11. According to some such embodiments, as shown generally in FIG. 4, the outer wall member 12 may define an emptying aperture 80. In such embodiments, the apparatus 1 may further comprise a door member 85 configured for selectively opening the emptying aperture 80 such that the sample S may be ejected from the first rotating surface 10 via the emptying aperture 80. As shown in FIG. 4, the door member 85 may open generally inwardly (towards the divider member 30) so as to divert the sample S outward through the emptying aperture 80 the first rotating member 10 carries the particles of the sample S towards the open door member 85.

Some additional apparatus embodiments of the present invention may provide an integrated scanning apparatus 1 (see FIGS. 5A and 5B, for example) further comprising a sensor device 101 operably engaged and/or selectively movable with respect to the various apparatus 1 components described herein. For example, as shown in FIG. 5B, the sensor device 101 may comprise, in some embodiments, an NIR spectrometer 101 operably engaged with a pintle 102 or other rotatable mounting member for suspending the sensor device 101 substantially above the scanning chamber 35 defined by the apparatus 1. For example, in one embodiment, the sensor device 101 comprises a Cora 45 NIR Spectrometer system (including integrated controller elements and software for scanning agricultural products), available from Carl Zeiss, AG. In other embodiments, the sensor device 101 may comprise a variety of sensors capable of emitting and/or detecting energy emitted and/or reflected and having a variety of wavelengths including, but not limited to: infrared, ultraviolet, and visible light. For example, in some embodiments, the sensor device 101 may comprise a camera that operates in the visible light spectrum.

As shown in FIG. 5A, the pintle 102 may allow for the selective rotation of the sensor device 101 up and away from the remaining portions of the apparatus 1 (including, for example, a radially outer wall 12, first rotating surface 10, second rotating surface 20, dividing member 30, and the radially inner wall 30, as described further herein). According to such embodiments, the pintle 102 may thus allow a user to selectively move the sensor device 101 away from the remaining portions of the apparatus 1 such that the sample S may be easily loaded into the apparatus 1 (and/or dropped onto the first rotating surface 10 thereof). Once the sample S is loaded into the apparatus 1, a user may swing the sensor device 101 into position relative to the scanning chamber 35 defined by the apparatus 1 as shown generally in FIG. 5B. It should be understood that multiple sensor devices 101 may be operably engaged with corresponding multiple pintles 102 such that a series of sensor devices 101 may be positioned adjacent to the length of the scanning chamber 35 such that a second set of scans may be obtained for each presented surface of each particle of the sample S as it is moved through the scanning chamber 35 by the counter-rotation of the first and second rotating surfaces 10, 20.

While the apparatus 1 embodiments shown in FIGS. 5A and 5B generally depict an "all-in-one" sensor device 101 (i.e. an NIR spectrometer and associated processing elements) carried in a single housing, it should be understood that various apparatus 1 embodiments of the present invention may also comprise sensor devices 101 wherein only portions of the sensor device 101 are suspended relative to the scanning chamber 35. For example, in some embodiments, only a lamp and a corresponding receiver element may be suspended above the scanning chamber 35 and the remaining power, processing, optical elements and/or control elements of the sensor device 101 may be in communication with such elements but housed separately and/or remotely from the lamp and/or corresponding receiver elements of the sensor device 101. Such embodiments, may allow the scanning elements (i.e. lamps and corresponding receiver elements) of the sensor device 101 to be permanently and/or semi-permanently suspended relative to the scanning chamber 35 (due to their relatively small size) such that a user may load the sample particles into the apparatus 1 without the need to move the sensor device 101 relative to the scanning chamber 35 (as shown in FIGS. 5A and 5B for example). Such embodiments may also allow for multiple scanning elements (corresponding to multiple sensor devices 101, for example) to be positioned substantially adjacent the scanning chamber 35 without the need to crowd and/or substantially cover the other portions of the apparatus 1 (i.e. portions of the apparatus 1 outside the scanning chamber 35).

Other embodiments of the present invention further provide a method for presenting a sample S comprising a plurality of sample particles to a scanning field defined by a sensor device 101. In one embodiment, shown schematically in FIG. 1, the method comprises steps for rotating a first rotating surface 10 about a central axis 5 in a first direction 11. The method further comprises rotating a second rotating surface 20 about the central axis 5 in a second direction 21 opposite the first direction 11. As shown in FIG. 1, the second rotating surface 20 may be disposed radially inward from the first rotating surface 10. Furthermore, as described herein with respect to various apparatus 1 embodiments, the second rotating surface 20 may comprise an inner wall member 25 extending substantially vertically from a radially-inward edge of the second rotating surface 20.

In some embodiments, the method further comprises fixing a dividing member 30 radially between the first rotating surface 10 and the second rotating surface 20. As shown in FIG. 1, the dividing member 30 may be provided with an entrance end 31 and an exit end 32. The dividing member 30 may be configured to cooperate with the second rotating surface 20 and the inner wall member 25 thereof to define a scanning chamber 35 configured to contain the scanning field of the sensor device 101. The method may further comprise directing the sample S from the first rotating surface 10 to the second rotating surface 20 and into the scanning chamber 35 using an entrance gate 40 disposed adjacent to the entrance end 31 of the dividing member 30. In some embodiments, the entrance gate 40 may be disposed substantially vertically with respect to the first rotating surface 10. In order to re-circulate the various particles of the sample S about the dividing member 30 as shown generally in FIG. 1, the method may further comprise directing the sample S from the second rotating surface 20 to the first rotating surface 10 and out of the scanning chamber 35 using an exit gate 50 disposed adjacent to the exit end 32 of the dividing member 30. As described above with respect to the entrance gate 40, the exit gate 50 may be disposed substantially vertically with respect to the second rotating surface 20. Thus, using the method embodiments described herein, the plurality of sample particles of the sample S may be continuously reoriented relative to the scanning field defined by the sensor device 101 as the sample S is re-circulated about the dividing member 30 and directed into and out of the scanning chamber 35 defined thereby.

As shown generally in FIG. 3, some method embodiments of the present invention may further comprise arranging the plurality of particles in the sample S to form a substantially flat upper sample surface as the sample S is directed through the scanning chamber 35. In such method embodiments, the arranging step may be accomplished using a leveling device 60 operably engaged between the divider member 30 and the inner wall member 12. As described herein with respect to the various apparatus 1 embodiments, the leveling device 60 may be suspended above the second rotating surface 20 by a support member 61. Furthermore, the leveling device 60 may be selectively movable with respect to the support member 61 such that the level of the sample S may be adjusted by moving the lower edge of the leveling device 60 relative to the second rotating surface 20.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for presenting a sample comprising a plurality of sample particles to a scanning field defined by a sensor device, the method comprising:
    directing the sample into a scanning chamber configured to contain at least a portion of the scanning field of the sensor device;
    subjecting the sample to different relative velocities; and
    redirecting the sample into the scanning chamber such that the plurality of sample particles of the sample are reoriented relative to the scanning field defined by the sensor device.

2. The method according to claim 1, wherein subjecting the sample to different relative velocities comprises moving at least a portion of the sample past a substantially stationary object.

3. The method according to claim 1, wherein subjecting the sample to different relative velocities comprises subjecting portions of the sample to at least first and second velocities.

4. The method according to claim 3, wherein the first and second velocities have different relative speeds.

5. The method according to claim 3, wherein the first and second velocities have different relative directions.

6. The method according to claim 3, wherein the first and second velocities comprise velocities having substantially the same direction and different speeds.

7. The method according to claim 3, wherein the first and second velocities comprise velocities having substantially the same speed and different directions.

8. A method of processing a sample comprising a plurality of sample particles, the method comprising:
 directing the sample into a scanning chamber configured to contain at least a portion of the scanning field of the sensor device;
 subjecting the sample to different relative velocities;
 redirecting the sample into the scanning chamber such that the plurality of sample particles of the sample are reoriented relative to the scanning field defined by the sensor device; and
 measuring at least one trait of the sample with the sensor device.

9. The method according to claim 8, wherein the least one trait is selected from the group consisting of:
 oil content of the sample particles;
 amino acid content of the sample particles;
 protein content of the sample particles;
 protein quality of the sample particles;
 high total fermentables of the sample particles;
 a presence of mold in the sample particles;
 a presence of mycotoxins in the sample particles; and
 combinations thereof.

10. The method according to claim 8 further comprising collecting sample data based at least in part on the at least one trait.

11. The method according to claim 8 further comprising evaluating the sample based at least in part on the at least one trait.

12. The method according to claim 8 further comprising selecting samples having desired genotypes based at least in part on the at least one trait.

\* \* \* \* \*